(12) United States Patent  
Choe et al.

(10) Patent No.: US 11,515,043 B1  
(45) Date of Patent: Nov. 29, 2022

(54) METHOD AND DEVICE FOR HAIR LOSS PREDICTION AND PERSONALIZED SCALP CARE

(71) Applicant: LULULAB INC., Seoul (KR)

(72) Inventors: Yongjoon Choe, Seoul (KR); Sangwook Yoo, Seoul (KR)

(73) Assignee: LULULAB INC., Seoul (KR)

( * ) Notice: Subject to any disclaimer, the term of this patent is extended or adjusted under 35 U.S.C. 154(b) by 0 days.

(21) Appl. No.: 17/732,771

(22) Filed: Apr. 29, 2022

(30) Foreign Application Priority Data

Nov. 5, 2021 (KR) .......................... 10-2021-0151729  
Mar. 17, 2022 (KR) .......................... 10-2022-0033603

(51) Int. Cl.
 G16H 50/20 (2018.01)
 G16H 20/00 (2018.01)
 (Continued)

(52) U.S. Cl.
 CPC .......... G16H 50/20 (2018.01); A61M 5/3295 (2013.01); G06T 7/0012 (2013.01); G16H 20/00 (2018.01);
 (Continued)

(58) Field of Classification Search
 None
 See application file for complete search history.

(56) References Cited

U.S. PATENT DOCUMENTS

| | | | |
|---|---|---|---|
| 2017/0032223 A1* | 2/2017 | Zingaretti | A61B 5/486 |
| 2018/0214072 A1* | 8/2018 | Zingaretti | A61B 5/448 |

FOREIGN PATENT DOCUMENTS

| | | |
|---|---|---|
| KR | 10-1539267 B1 | 7/2015 |
| KR | 10-2213447 B1 | 2/2021 |

(Continued)

OTHER PUBLICATIONS

Translation of KR20220021919A (Year: 2022).*

(Continued)

Primary Examiner — Manuel A Mendez  
(74) Attorney, Agent, or Firm — Sughrue Mion, PLLC

(57) ABSTRACT

In accordance with various embodiments, provided is a scalp management service provision server for providing a hair loss prevention service and scalp care service for a user, including: a DB management unit interlocked with the scalp management service provision server and configured to obtain a scalp image of the user from a scalp care device including a camera; a scalp condition diagnosis unit configured to determine a scalp condition of the user based on the obtained scalp image; a hair condition diagnosis unit configured to determine a hair condition of the user based on the obtained scalp image; a hair loss diagnosis unit configured to provide a current hair loss progress degree of the user and a hair loss prediction simulation of the user based on the scalp condition and the hair condition; a scalp care solution provision unit configured to provide information about a scalp analysis result and hair analysis result of the user through a user terminal of the user and to determine a scalp care product for the user from among a number of scalp care products included in a scalp care product DB; and a remote care device control unit configured to remotely control the scalp care device with a control value determined according to the scalp analysis result and hair analysis result of the user.

5 Claims, 7 Drawing Sheets

(51) Int. Cl.
*G16H 40/67* (2018.01)
*A61M 5/32* (2006.01)
*G06T 7/00* (2017.01)

(52) U.S. Cl.
CPC ..... *G16H 40/67* (2018.01); *A61M 2205/3313* (2013.01); *A61M 2205/3561* (2013.01); *A61M 2205/3584* (2013.01); *G06T 2207/30088* (2013.01)

(56) References Cited

FOREIGN PATENT DOCUMENTS

KR        10-2284773 B1    8/2021
KR   10-2022-0027910 A    3/2022

OTHER PUBLICATIONS

Translation of KR102284773B1 (Year: 2021).*
Translation of KR102213447B1 (Year: 2021).*
Translation of KR101539267B1 (Year: 2015).*

* cited by examiner

[FIG. 6]
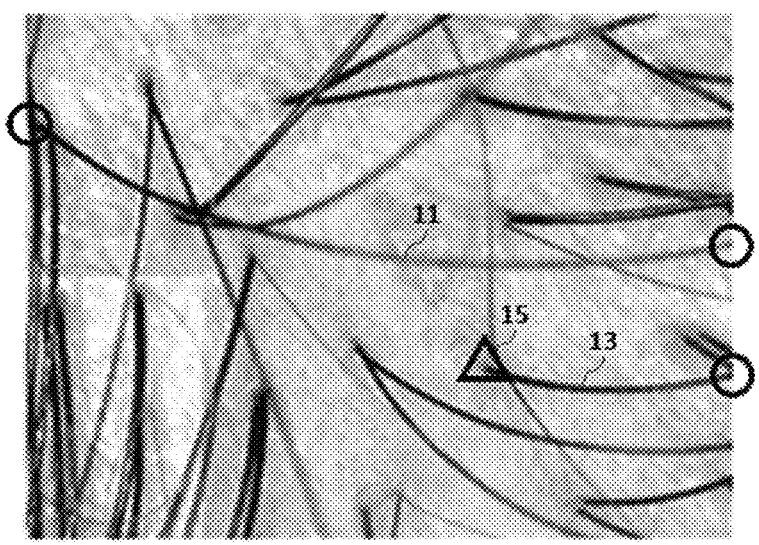

[FIG. 7]
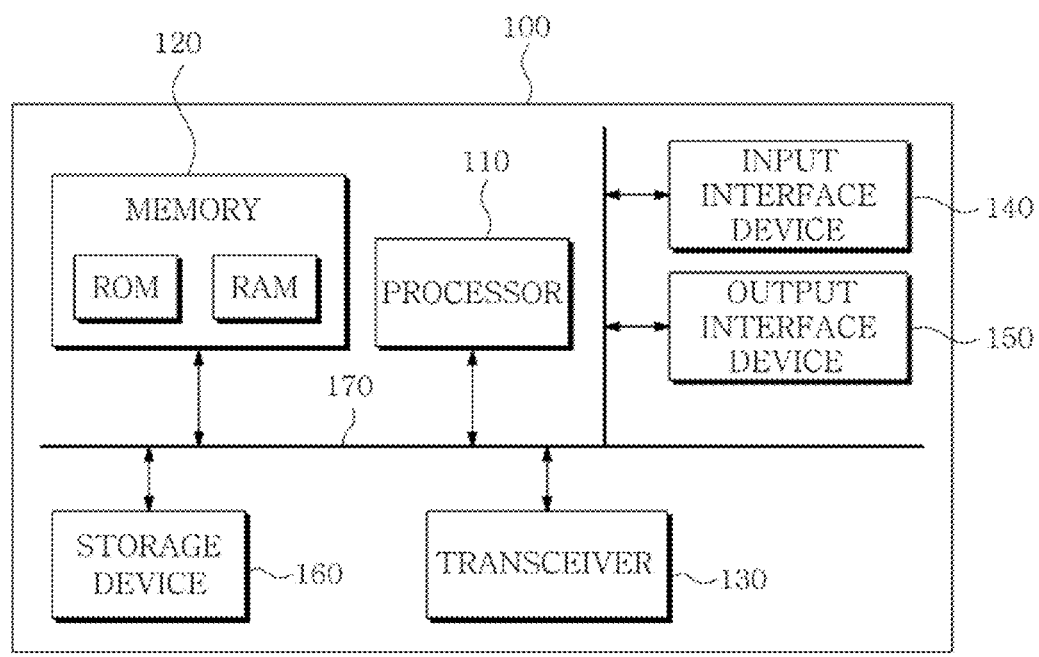

METHOD AND DEVICE FOR HAIR LOSS PREDICTION AND PERSONALIZED SCALP CARE

CROSS REFERENCE TO RELATED APPLICATIONS

This application claims priority to Application No. KR 10-2021-0151729 filed in Korea on Nov. 5, 2021, and Application No. 10-2022-0033603 filed in Korea on Mar. 17, 2022. The entire contents of each application is hereby incorporated by reference.

FIELD OF INVENTION

The present invention is a technology related to scalp analysis and care, and more particularly to a method and device for AI-based hair loss prediction and personalized scalp care.

BACKGROUND OF INVENTION

Hair loss is a disease with a high prevalence, occurring at a rate of 1 in 4 adults. Hair loss is not a disease that threatens a person's life or restricts the behavior of the human body, but it is a disease that significantly lowers an individual's social function due to a psychological problem induced thereby. Individual stress due to hair loss is quite large, negative factors such as lack of confidence due to hair loss and interpersonal phobia are considerable, and the loss of social opportunity cost is also considerable. Hair loss is recognized as a very serious problem by the standards of modern people who value appearance, and the hair loss-related market has been growing steadily since the 1990s.

In general, hair loss can be divided into male pattern hair loss and female pattern hair loss, which are progressive diseases that gradually progress due to genetic predisposition, and can be divided into alopecia areata and telogen hair loss that suddenly progresses due to specific factors. Male pattern hair loss and female pattern hair loss due to genetic predisposition are processes in which thick hair gradually becomes thinner and eventually becomes invisible hair. This type of hair loss appears to progress over a long period of time.

On the other hand, alopecia areata is a disease in which immune cells attack one's own hair follicles due to an abnormality in the autoimmune system so that hair suddenly falls out. In addition, telogen hair loss is a disease in which hair loss occurs suddenly due to abnormalities in the endocrine system, drug side effects, chronic nutritional imbalance, severe external stimuli, and the like. Such alopecia areata and telogen hair loss are occurring in a relatively short time compared to hair loss caused by genetic predisposition.

As such, hair loss can be caused by various factors, so it is important to provide customized diagnosis and treatment for each hair loss patient. In particular, in the case of alopecia areata or telogen hair loss, not hair loss due to a genetic predisposition, diagnosis and treatment through accurate diagnosis of the time of hair loss and area of hair loss are essentially required.

However, it is difficult to provide an accurate diagnosis and treatment of hair loss to a patient because a doctor visually diagnoses a hair loss area based on a patient's scalp image and calculates the hair loss area.

SUMMARY OF INVENTION

Technical Problem to be Solved

Therefore, the present invention has been made in view of the above problems, and it is one object of the present invention to provide a method and device for analyzing the condition of the scalp or hair based on AI and a method and device for hair loss prediction and personalized scalp care based on the analysis.

Technical Solution

In accordance with an aspect of the present invention, the above and other objects can be accomplished by the provision of a scalp management service provision server for providing a hair loss prevention service and scalp care service for a user, including: a DB management unit interlocked with the scalp management service provision server and configured to obtain a scalp image of the user from a scalp care device including a camera; a scalp condition diagnosis unit configured to determine a scalp condition of the user based on the obtained scalp image; a hair condition diagnosis unit configured to determine a hair condition of the user based on the obtained scalp image; a hair loss diagnosis unit configured to provide a current hair loss progress degree of the user and a hair loss prediction simulation of the user based on the scalp condition and the hair condition; a scalp care solution provision unit configured to provide information about a scalp analysis result and hair analysis result of the user through a user terminal of the user; and a remote care device control unit configured to remotely control the scalp care device with a control value determined according to the scalp analysis result and hair analysis result of the user.

In accordance with various embodiments, the scalp care device may include a photographing part provided on one side of the scalp care device in a longitudinal direction and provided with a camera capable of photographing scalp of the user; a care part provided in another area opposite to the side of the scalp care device in a longitudinal direction and configured to take care of the scalp; and a grip part provided between the photographing part and the care part for gripping by the user, wherein the care part includes a needle holder including a plurality of needles; and an ampoule container, and the grip part includes a photographing button for obtaining a scalp image of the user through the photographing part, wherein a distal end portion of the grip part protrudes with respect to a central portion of the grip part.

In accordance with various embodiments, the hair loss diagnosis unit may determine a hair loss improvement result predicted when the user performs recommended guidance provided through the scalp care solution provision unit, and determine a worsened hair loss result of the user predicted when the recommendation guidance is not performed, wherein the recommended guidance provides information about life guidance and scalp care products.

In accordance with various embodiments, the hair loss diagnosis unit may determine first users having the same hair loss type as the user, determine hair loss progress rates of the user and first users based on scalp images obtained from the user and the first users every specific interval, determine second users based on the determined hair loss progress rates, and predict a worsened hair loss result and hair loss improvement result at a future time point of the user based on big data for the second users.

In accordance with various embodiments, the scalp care solution provision unit may chronologically list the user's scalp state images, provide the listed scalp condition images to the user terminal, and calculate composite scores for a scalp condition corresponding to the scalp condition images, wherein individual scores are calculated for each individual item for each of a scalp keratin state, scalp pore state, hair thickness, hair number, and hair density of the user, the summed scores of the calculated individual scores are determined as the composite scores, and the determined composite scores are provided to the user terminal.

In accordance with various embodiments, the hair condition diagnosis unit may pre-process the obtained scalp image through contrast stretching and calculate the density of hair through the number of hairs included in an image frame constituting the pre-processed scalp image, wherein the outlines of hairs are detected through edge detection within the image frame, and the number of hairs is calculated by excluding hairs touching two outer lines among outer lines constituting the image frame among the hairs whose outlines are detected and by counting hairs touching one outer line of the outer lines constituting the image frame among the hairs whose outlines are detected.

In accordance with various embodiments, the scalp management service provision server further includes a hair loss progression similarity calculation unit, wherein the hair loss progression similarity calculation unit calculates a hair loss progression similarity between the first users and the user based on the hair loss progression rate. Here, a hair increase/decrease amount and a hair change degree may be calculated for each of the user and the first users based on the hair conditions collected for the user and the first users, and the similarity of hair loss progress between the first users and the user may be calculated based on the calculated hair increase/decrease amount and hair change degree. The hair loss diagnosis unit may determine, among the first users, users whose calculated hair loss progression similarity is equal to or greater than a reference threshold value as the second users.

In accordance with various embodiments, the hair increase/decrease amount and the hair change degree are calculated based on scalp images obtained for each specific period, and calculated according to the following equations:

$$C_h = \frac{H_s \cdot H_o}{\|H_s\| \cdot \|H_o\|}$$

$$H_x = (x1, x2, \ldots, xn), H_o = (y1, y2, \ldots, yn)$$

$$\|H_a\| = \sqrt{\sum_{i=1}^{n}(xi)^2},$$

$$\|H_o\| = \sqrt{\sum_{i=1}^{n}(yi)^2}$$

wherein $H_a$ denotes a reference hair increase/decrease amount of the user, $H_o$ denotes the hair increase/decrease amount of each of the first users, and $C_h$ denotes an increase/decrease correlation degree between the reference hair increase/decrease amount of the user and the hair increase/decrease amount of each of the first users, $$DIS = \sqrt{\sum_{i=1}^{n}(pi - qi)^2}$$

$$R_a = (p1, x2, \ldots, pn), R_o = (q1, q2, \ldots, qn)$$

where $R_a$ denotes a reference hair change degree of the user, and $R_o$ denotes a hair change degree of each of the first users, and the hair loss progression similarly is calculated through the following equation:

$$P_h = C_h^k + \frac{DIS_\sigma}{DIS - DIS_\mu}^{1-k}$$

where $P_h$ denotes the hair loss progression similarity, k is a weighting coefficient for determining a weight between an increase/decrease correlation degree ($C_h$) and the Euclidean distance (DIS) and is an integer between 0 and 1, DISμ is an average value of calculated Euclidean distances for the first users, and DISσ is a standard deviation of the calculated Euclidean distances for the first users.

In accordance with various embodiments, the scalp care solution provision unit calculates a composite score change through the following equation, $$S = \sum_{i=1}^{i=n}((i_a - i_b) \times w_i)$$

where S denotes a change in the composite scores, n denotes the number of individual items for calculating a composite score on a scalp condition, $i_a$ denotes a score of a i-th item for calculating a composite score for a scalp condition corresponding to the first image, in denotes a score of a i-th item for calculating a composite score for a scalp condition corresponding to the second image, and $w_i$ denotes a weight for a i-th item.

Effect of Invention

In accordance with various embodiments of the present specification, the present invention can serve as a next-generation scalp health care consultant capable of being systematically preventing hair loss and preforming continuous hair health management by diagnosing a scalp condition using a mobile app and checking a hair loss progression simulation.

In addition, according to various embodiments, a user can easily accurately identify the progress of his/her hair loss at home and perform appropriate management.

In addition, according to various embodiments, a user can perform the most appropriate management for a current state by automatically setting the length of a needle and the amount of an ampoule which are suitable for each scalp location through an AI algorithm according to a diagnosis result.

In addition, according to various embodiments, a next-generation scalp health care service that can systematically prevent hair loss and continuously manage hair health can be provided.

Further, various effects directly or indirectly identified through the present specification can be provided.

BRIEF DESCRIPTION OF DRAWINGS

FIG. 6 exemplarily illustrates the determination of a hair condition with a hair condition diagnosis unit.

FIG. 7 illustrates a hardware configuration of the scalp management service provision server 100 of FIG. 1.

BEST MODE

Figure 1:
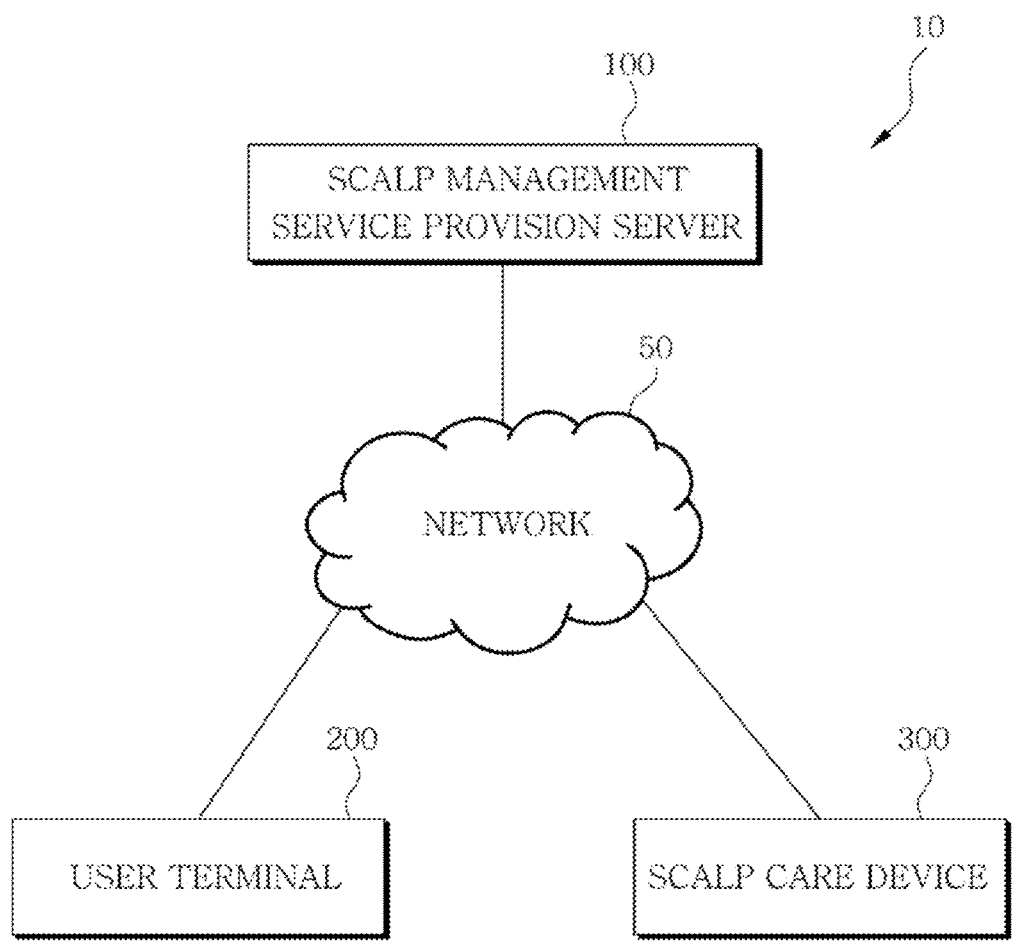
FIG. 1 illustrates a scalp care service provision system according to an embodiment.

Since the present invention may be applied with various modifications and may have various embodiments, exemplary embodiments and drawings of the present invention are intended to be explained and exemplified. However, these exemplary embodiments and drawings are not intended to limit the embodiments of the present invention to particular modes of practice, and all changes, equivalents, and substitutes that do not depart from the spirit and technical scope of the present invention should be understood as being encompassed in the present invention. Like reference numerals refer to like elements in describing each drawing.

The terms such as "first," "second," "A" and "B" are used herein merely to describe a variety of constituent elements, but the constituent elements are not limited by the terms. The terms are used only for the purpose of distinguishing one constituent element from another constituent element. For example, a first element may be termed a second element and a second element may be termed a first element without departing from the teachings of the present invention. The term "and/or" includes any or all combinations of one or more of the associated listed items.

It should be understood that when an element is referred to as being "connected to" or "coupled to" another element, the element may be directly connected or coupled to the other element or intervening elements may be present. In contrast, when an element is referred to as being "directly connected to" or "directly coupled to" another element, there are no intervening elements present.

The terms used in the present specification are used to explain a specific exemplary embodiment and not to limit the present inventive concept. Thus, the expression of singularity in the present specification includes the expression of plurality unless clearly specified otherwise in context. Also, terms such as "include" ox "comprise" should be construed as denoting that a certain characteristic, number, step, operation, constituent element, component or a combination thereof exists and not as excluding the existence of or a possibility of an addition of one or more other characteristics, numbers, steps, operations, constituent elements, components or combinations thereof.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and will not be interpreted in an idealized ox overly formal sense unless expressly so defined herein.

Hereinafter, the present invention will be described in detail by explaining exemplary embodiments of the invention with reference to the attached drawings. [43] FIG. 1 illustrates a scalp care service provision system 10 according to an embodiment. Referring to FIG. 1, the scalp care service provision system 10 may include a scalp management service provision server 100, a user terminal 200, a scalp care device 300, and the like. Operations described below may be performed or implemented through a platform (e.g., a web page and/or a beauty-health care application) controlled by the scalp management service provision server 100. In other words, the scalp management service provision server 100 may provide a website where a user can access the scalp management service provision server 100 through a network using the user terminal 200 to input, register, and output various information; and an application capable of inputting, registering, and outputting various information by being installed and executed in the user terminal 200.

The scalp management service provision server 100 may receive scalp condition information for each user and hair loss information for each user, and may store the received scalp condition information for each user and the received hair loss information for each user in a DB management unit 101. Whenever receiving new scalp condition information and hair loss information, the scalp management service provision server 100 may convert the received information into a database, upgrade, and store in the DB management unit 101.

The scalp management service provision server 100 may analyze a scalp condition and hair condition based on artificial intelligence (AI) deep learning technology and may predict hair loss by analyzing four key items of user's scalp health, including the types of hair loss, based on the analyzed scalp condition and hair condition, and the like. The scalp management service provision server 100 may provide a personalized scalp care service according to the diagnosis result. The scalp management service provision server 100 may inquire about a scalp condition diagnosis result for each user based on scalp image data measured through the scalp care device 300 (e.g., a handy all-in-one device), may manage data history, and may recommend a customized product.

The scalp management service provision server 100 may automatically set the needle length and ampoule amount of the scalp care device 300 suitable for each scalp position by using an AI algorithm according to the diagnosis result on the scalp condition.

A user may check a simulation of hair loss as well as the diagnosis result of the scalp condition and the history of the scalp condition, through the user terminal 200 or a mobile application implemented through the user terminal 200.

The user terminal 200 may be a communicationable desktop computer, a laptop computer, a notebook, a smart phone, a tablet PC, a mobile phone, a smart watch, a smart glass, an e-book reader, a portable multimedia player (PMP), a portable game console, a navigation device, a digital camera, a digital multimedia broadcasting (DMB) player, a digital audio recorder, a digital audio player, a digital video recorder, a digital video player, and a personal digital assistant (PDA), or the like.

Each of the scalp management service provision server 100 and the user terminal 200 may be connected to the communication network 50 to transmit and receive data between each other through the communication network 50. For example, various types of wired or wireless networks such as Local Area Network (LAN), Metropolitan Area Network (MAN), Global System for Mobile Network (GSM), Enhanced Data GSM Environment (EDGE), High Speed Downlink Packet Access (HSDPA), Wideband Code Division Multiple Access (W-CDMA), Code Division Multiple Access (CDMA), Time Division Multiple Access (TDMA), Bluetooth, Zigbee, Wi-Fi, Voice over Internet Protocol (VoIP), LTE Advanced, IEEE802.16m, wireless MAN-Advanced, HSPA+, 3GPP Long Term Evolution (LTE), mobile WiMAX (IEEE 802.16e), formerly EV-DO Rev. C (UMB), flash-OFDM, iBurst and MBWA (IEEE 802.20) systems, HIPERMAN, Beam-Division Multiple Access (BDMA), World Interoperability for Microwave Access (Wi-MAX) and 5G may be used as the communication network 50.

Figure 2:
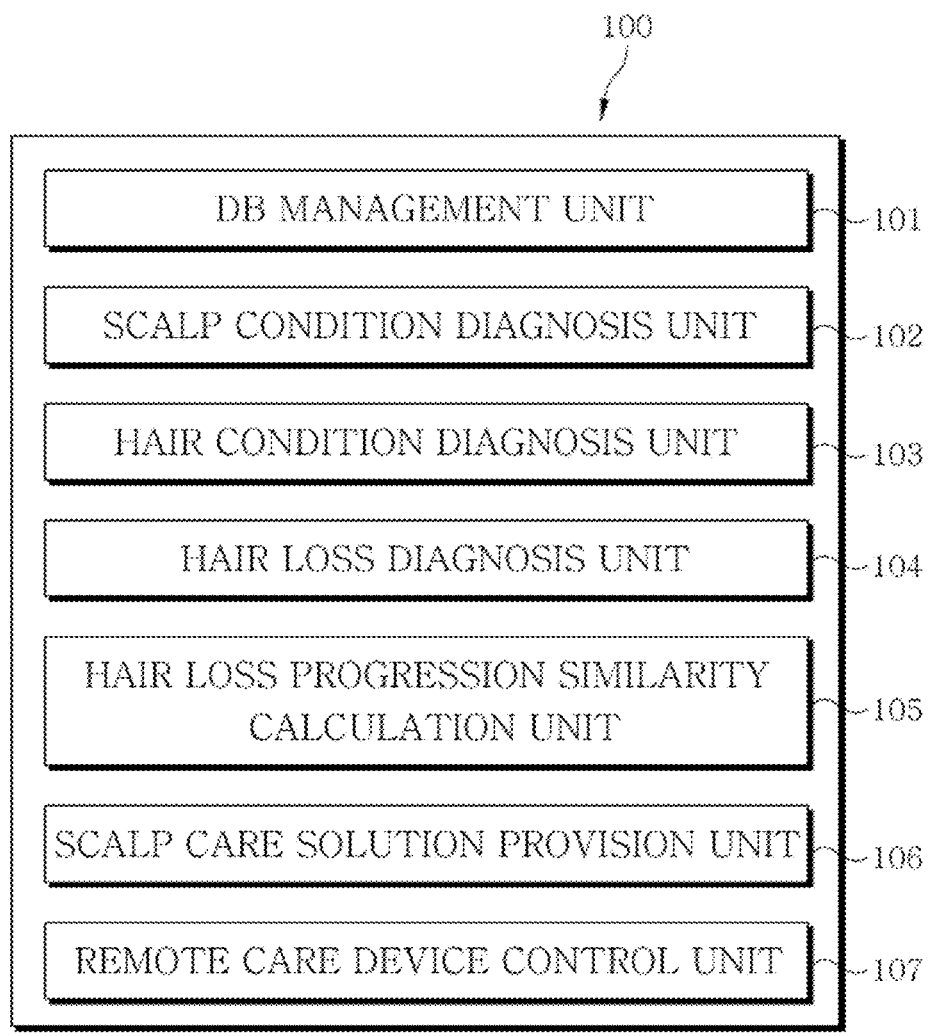
FIG. 2 illustrates main components of the scalp management service provision server of FIG. 1.

FIG. 2 illustrates main components of the scalp management service provision server 100.

The scalp management service provision server 100 may include a DB management unit 101, a scalp condition diagnosis unit 102, a hair condition diagnosis unit 103, a hair loss diagnosis unit 104, a scalp care solution provision unit 106, a remote care device control unit 107, and the like.

The DB management unit 101 may store or manage data on a user's scalp image obtained through the scalp care device 300; and data classified according to a scalp condition, a hair condition, a hair loss type, a hair loss progress stage, etc. based on analysis of the user's scalp image. In addition, the DB management unit 101 may store or manage data on various types of scalp care products.

The scalp condition diagnosis unit 102 ray determine a user's scalp condition or scalp characteristics corresponding to the time at which the scalp image is obtained, based on the user's scalp image obtained through the scalp care device 300. For example, the scalp condition or scalp characteristics may include the moisture, oil, sebum, pH Level, sensitivity, elasticity, wrinkles, skin tone, pore state, pigmentation, keratin state, etc. of the scalp. The scalp condition diagnosis unit 102 may obtain an image of the user's scalp through a separate measurement device (e.g., a measuring mask, or a camera included in the user terminal 200) in addition to the scalp care device 300.

The scalp condition diagnosis unit 102 may divide the obtained user's scalp image into a plurality of scalp regions, and determine scalp characteristics for each of the plurality of divided scalp regions. The plurality of scalp regions may include a front scalp, a rear scalp, a left-side scalp, a right-side scalp, a forehead, and the like. The scalp condition diagnosis unit 102 may determine user's scalp characteristics based on the moisture, oil, sebum, pH level, sensitivity, wrinkles, skin tone, pore condition, pigmentation, keratin condition, etc. of the scalp for each of the plurality of scalp regions.

The scalp condition diagnosis unit 102 may receive information for each item of at least one of oily, seborrheic, dry, dandruff, sensitive, inflammatory, alopecia, etc. classified for each user from the DB management unit 101, and may execute learning and reading using the inception V3 model as a deep learning algorithm by utilizing big data information of the DB management unit 101 for the received information, and may derive a final result diagnosis with a specific precise diagnosis by inferring the image through additional retraining of a scalp image set. For example, the scalp condition diagnosis unit 102 may use tensorflow when using Google's deep learning model and utilize the inception V3 model to classify the user's scalp condition through retraining.

The scalp condition diagnosis unit 102 may collect data by learning the scalp image as a deep learning step by artificial intelligence (AI) analysis utilizing big data information on the received scalp image, and may classify (label) the collected learning data. The scalp condition diagnosis unit 102 may classify and verify the collected data into training data and test data (7:3), Learn and verify and may derive an inference model (Convolutional Neural Network, CNN).

The hair condition diagnosis unit 103 may diagnose or determine the hair condition of the user with various items, such as the thickness of hair, the number of hairs, and the density of hair, based on the scalp image obtained through the scalp care device 300. The scalp image may be analyzed with more than 2G items, such as the thickness of hair, the number of hairs, the density of hair, based on artificial intelligence technology, and the analyzed data may be reprocessed by 4 items including a hair loss type, a hair loss progression stage, and the like.

The hair loss diagnosis unit 104 may determine a user's hair loss type (e.g., M-shaped hair loss, circular hair loss, side hair loss, frontal hair loss, back hair loss, etc.) and a user's current hair loss progress stage (e.g., initial stage, intermediate stage) based on the obtained scalp image. The hair loss type may be divided into about 40 types according to the acquired scalp image, and the hair loss progression stage may be divided into at least 5 stages.

The hair loss diagnosis unit 104 ray predict not only a current hair loss progress stage, but also hair loss progress corresponding to a future time point. The hair loss diagnosis unit 104 may visualize the predicted progress of hair loss and may display the visualized hair loss progress and information about the thickness of hair, the number of hairs, the density of hair, and the oil and moisture level of the scalp corresponding to the progress through the user terminal 200. In other words, the hair loss diagnosis unit 104 may determine the current hair loss progress, hair loss possibility, and future hair loss prediction degree, and the like. of the user based on at least one of a user's scalp condition determined through the scalp condition diagnosis unit. 102, a user's hair condition determined through the hair condition diagnosis unit 103 and questionnaire information obtained from the user terminal 200.

In one embodiment, the hair loss diagnosis unit 104 may provide a simulation result of converting the scalp image, taken from multiple angles by the user using the scalp care device 300 into big data GAN deep learning technology to predict when hair loss has occurred, to the user terminal 200. For example, the questionnaire information may be information about daily average hat wearing time, daily average number of hair washings, oil and moisture characteristics of hair (e.g., oily, dry, neutral, etc.), whether or not hair loss in the immediate family, type of hair loss (e.g., M-shaped hair loss, circular hair loss, side hair loss, frontal hair loss, back hair loss, etc.), circulatory disorder, stress diagnosis information, digestive function disorder, and the like.

In one embodiment, the hair loss diagnosis unit 104 may predict hair loss improvement result of the user in the future based on a user's scalp condition, a user's hair condition and questionnaire information, as well as big data regarding a scalp care routine and management method of other people with the same hair loss type as the user. The scalp care routine and management method may be recommended guidance provided through the scalp care solution provision unit 106. In other words, the hair loss diagnosis unit 104 may provide the user terminal 200 with a simulation result for predicting when the user's hair loss is improved.

When using the big data of other people, the hair loss diagnosis unit 104 may first determine first users having the same hair loss type as the user among users stored in the DB management unit 101. The hair loss diagnosis unit 104 may determine a plurality of second users having similar rates of hair loss to the user among the first users. In other words, the hair loss diagnosis unit 104 may determine, among the first users, users whose similarity of hair loss progress with the user is above the reference threshold as the second users, and may predict the hair loss improvement result of the user in the future according to the recommended guidance provided through the scalp care solution provision unit 106 based on the big data for the second users.

The hair loss diagnosis unit 104 may determine the rate of hair loss of the user and/or the first users based on the scalp image of each of the user and/or the first users every specific period (e.g., 1 month). The hair loss diagnosis unit 104 may calculate the hair loss progression similarity between the first users and the user through a hair loss progression similarity calculation unit 105, and determine the second users based on the calculated hair loss progression similarity.

The hair loss progression similarity calculation unit 105 may calculate the hair sensitivity and hair change degree for each of the first users based on hair conditions collected for the first users having the same hair loss type. In this case, a hair condition serving as basic data may be determined as data within the last 2 years or within the last 1 year. The hair condition may be expressed as the number of hairs of the user analyzed by the hair condition diagnosis unit 103 based on the user's scalp image. In this case, the hair sensitivity may be calculated using the 'gradient sign' of the number of hairs for each month. Hair sensitivity can be expressed as a vector. Here, a hair increase/decrease amount may be calculated using a 'gradient sign' of the number of hairs for each month. The hair increase/decrease amount may be expressed as a vector.

For example, if the number of hairs decreased (−), increased (+), decreased (−), decreased (−), decreased (−), and decreased (−) a hair increase/decrease amount from January to December, may be (−1, +1, −1, −1, −1, −1). As another example, if the number of hairs decreased (−), was the same (0), decreased (−), was the same (0), decreased (−), or the same (0) from January to December, a hair increase/decrease amount from January to December may be (−1, 0, −1, 0, −1, 0).

That is, the component value of the hair increase/decrease amount corresponding to the current month may be '−1' when the number of hairs in the current month is decreased compared to the previous month, the component value of the hair increase/decrease amount corresponding to the current month may be '0' when the number of hairs in the last month and the current month is the same, and the component value of hair increase/decrease amount corresponding to the current month may be '+1' when the number of hairs increases in the current month from the previous month.

Meanwhile, the hair change degree may be calculated using the 'size of the slope' of the number of hairs for each month. For example, if the number of hairs varies from −2, +1, −3, −2, −4, −1 from January to December, a hair change degree may be (2, 1, 3, 2, 4, 1). That is, a component value of the hair change degree corresponding to the current month may represent the number of changes in the hair.

The hair loss progression similarity calculation unit 105 may calculate an increase/decrease correlation ($C_h$) between the reference hair increase/decrease amount of the user and the hair increase/decrease amount of each of the first users based on Equation 1 below:

[Equation 1]

$$C_h = \frac{H_s \cdot H_o}{\|H_s\| \cdot \|H_o\|}$$

$$H_s = (x1, x2, \ldots, xn),$$

$$H_o = (y1, y2, \ldots, yn)$$

In Equation 1, $H_a$ denotes a reference hair increase/decrease amount of the user, $H_o$ denotes the hair increase/decrease amount of each of the first users, $C_h$ denotes an increase/decrease correlation degree between the reference hair increase/decrease amount of the user and the hair increase/decrease amount of each of the first users, and the molecular part denotes a dot product operation between the reference hair increase/decrease amount of the user and the hair increase/decrease amount of each of the first users.

The hair loss progression similarity calculation unit 105 may calculate the Euclidean distance (DIS) between a reference hair change degree of the user and a hair change degree of each of the first users based on Equation 2 below:

[Equation 2]

$$DIS = \sqrt{\sum_{i=1}^{n}(pi - qi)^2}$$

$$R_s = (p1, x2, \ldots, pn),$$

$$R_o = (q1, 2, \ldots, qn)$$

In Equation 2, $R_a$ denotes a reference hair change degree of the user, $R_o$ denotes a hair change degree of each of the first users, and the hair loss progression similarity calculation unit 105 may calculate a hair loss progression similarity ($P_h$) according to Equation 3 below using the increase/decrease correlation degree ($C_h$) and the Euclidean distance (DIS).

[Equation 3]

$$P_h = C_h^k + \frac{DIS_\sigma^{1-k}}{DIS - DIS_\mu}$$

Referring to Equation 3, k is a weighting coefficient for determining a weight between an increase/decrease correlation degree ($C_h$) and the Euclidean distance (DIS) and is an integer between 0 and 1, DISμ is an average value of calculated Euclidean distances for the first users, and DISσ is a standard deviation of the calculated Euclidean distances for the first users.

The hair loss diagnosis unit 104 may determine, among the first users, users having a hair loss progression similarity ($P_h$) equal to or greater than a reference threshold value as the second users.

The scalp care solution provision unit 106 may determine an ingredient and effect necessary for the user based on the user's scalp characteristics, and may determine recommendation products including the determined necessary ingredient and effect.

The scalp care solution provision unit 106 may determine the products based on product usage information of other people (e.g., second users) distinguished from the user as well as the determined necessary ingredient and effect. In other words, the scalp care solution provision unit 106 may determine the products based on products usage information of other users having a similar scalp condition to the user. The products may include cosmetics for scalp care, pharmaceuticals for scalp care, electronic devices for scalp care, medical devices for scalp care, and the like. Product usage information may include purchase reviews, a use period, a use frequency, a return status, and the like.

The scalp care solution provision unit 106 may provide the products suitable for a user's current condition based on product usage data, external environment, and lifestyle data of other users (e.g., second users) having a scalp condition similar to the user and may provide information about the determined products to the user terminal 200. The information about the products may include an online address where a scalp care product can be purchased, and information about the name, effect, price, and the like of the scalp care product.

The scalp care solution provision unit 106 may provide a scalp management solution through the user terminal 200 or an application, installed in the user terminal 200, based on the scalp condition data analyzed by artificial intelligence and the life log recorded by the user through a questionnaire. The scalp care solution provision unit 106 may provide recommended guidance (e.g., information about a recommended lifestyle and recommended eating habits, etc.) for improving a user's scalp condition and a user's hair condition.

The scalp care solution provision unit 106 may link the deep learning-based hair loss prediction results with activity data and/or health data collected in real time through a mobile application to provide optimal individual recommended guidance (e.g., customized guidance corresponding to a user's life pattern) according to a current scalp condition. It is possible to provide.

The scalp care solution provision unit 106 may provide a user's scalp diagnosis history through a mobile application installed in the user terminal 200. The scalp care solution provision unit 106 may continuously (or every preset period) obtain the questionnaire information from the user terminal 200, and generate user's Life-Log data according to the obtained questionnaire information. The scalp care solution provision unit 106 may help form a lifestyle for user's scalp health based on the generated lifelog data.

The scalp care solution provision unit 106 may store information about the user's (previous) scalp condition corresponding to each of the scalp image data, based on the user's scalp image data obtained from the scalp measurement device, and may provide the stored scalp condition information to the user terminal 200. The scalp image data may be obtained every preset period. The scalp care solution provision unit 106 may list images related to the user's skin condition in chronological order and provide the listed images to the user terminal 200 such that the user can directly feel a skin change due to the use of the scalp measurement device.

The scalp care solution provision unit 106 may calculate composite scores on the skin condition corresponding to the images, may generate a graph according to a score change between the calculated composite scores, and may provide the generated graph to the user terminal 200. The scalp care solution provision unit 106 may calculate an individual score for each item, such as scalp keratin condition, scalp pore condition, hair thickness, number of hairs, and hair density, of the user, and may determine a total score of the individual scores calculated for the respective item as a composite score for the skin condition.

The scalp care solution provision unit 106 may calculate a change in the composite scores between the images listed in chronological order, and may provide the information about the calculated composite score change to the user terminal 200. When calculating the composite score change, The scalp care solution provision unit 106 does not simply calculate a difference between a first composite score corresponding to a first image and a second composite score to corresponding to a second image, but may determine the weight of a first item corresponding to a lowest score in the first composite score as the highest and may determine the weight of a second item corresponding to a highest score in the first composite score as lowest. The scalp care solution provision unit 106 may calculate an individual score difference between items, may multiply the individual score difference by the weight, and may determine a total score of the individual score differences multiplied by the weight as a composite score change. The second image may be a first image acquired after a time point at which the first image is acquired under a preset condition (e.g., in time series or in order of scalp condition).

The scalp care solution provision unit 106 may calculate a change in the composite scores through Equation 4 below:

[Equation 4]

$$S = \sum_{i=1}^{i=n} ((i_a - i_b) \times w_i)$$

where S denotes a change in the composite scores, n denotes the number of individual items (scalp keratin condition, scalp pore condition, hair thickness, number of hairs, and hair density) for calculating a composite score on a scalp condition, $i_a$ denotes a score of a i-th item for calculating a composite score for a scalp condition corresponding to the first image, $i_o$ denotes a score of a i-th item for calculating a composite score for a scalp condition corresponding to the second image, and $w_i$ denotes a weight for a i-th item.

The remote care device control unit 107 may remotely control the scalp care device 300 to be driven. The remote care device control unit 107 may determine a control value for operating the scalp care device 300, and in particular, may provide an optimal control value for improving the user's scalp condition and/or hair condition to the user terminal 200. The remote care device control unit 107 may provide the control value to the user terminal 200, and the user may operate the scalp care device 300 with an optimal control value for improving the scalp condition based on the control value provided through the user terminal 200. The device 300 may be operated. The scalp care device control value may be at least a value related to the length of a needle, the amount of an ejected ampoule, the intensity of light, an operation time of the scalp care device, an operation mode of the scalp care device, and the like.

The remote care device control unit 107 may remotely control the scalp care device to be driven by the control value. In other words, the remote care device control unit 107 may control the scalp care device to be driven in a scalp care device operation mode, scalp care device operation time, and scalp care device operation intensity (e.g., light intensity) for improving the user's scalp condition.

The remote care device control unit 107 may determine an appropriate length of a needle and the amount of an ampoule according to a scalp thickness and scalp condition at each scalp location of a user. In other words, the remote care device control unit 107 may determine the appropriate length of a needle and the appropriate amount of an ampoule according to an epidermis thickness and dermis thickness at each location of the user's scalp and the condition of the scalp at each location. The remote care device control unit 107 may automatically set the length of the needle and the amount of the ampoule according to the skin thickness at each location through an AI algorithm based on a user's scalp dermal layer visualization image.

The remote care device control unit 107 may generate information about a scalp condition result (e.g., scalp condition diagnosis result) of each of the user's front scalp, rear scalp, left side scalp, and right side scalp, and the remote care device control unit 107 may control the scalp care device 300 to insert an ampoule containing an active ingredient corresponding to a user's scalp oil and moisture level into the user's scalp through hair loss type diagnosis based on the generated information.

In an embodiment, the remote care device control unit 107 may control the scalp care device such that a first ampoule amount is sprayed to the user's front scalp by a first length of the needle when a button of the scalp care device is pressed once, may control the scalp care device such that a second ampoule amount is sprayed to the user's rear scalp by a second length of the needle when the button of the scalp care device is pressed twice, may control the scalp care device such that a third ampoule amount is sprayed to the user's left side scalp by a third length of the needle when the button of the scalp care device is pressed three times, and may control the scalp care device such that a fourth ampoule amount is sprayed to the user's right side scalp by a fourth length of the needle when the button of the scalp care device is pressed four times. The first length, the second length, the third length, and the fourth length may have different values. The first ampoule amount, the second ampoule amount, the third ampoule amount, and the fourth ampoule amount may have different values.

Figure 3:
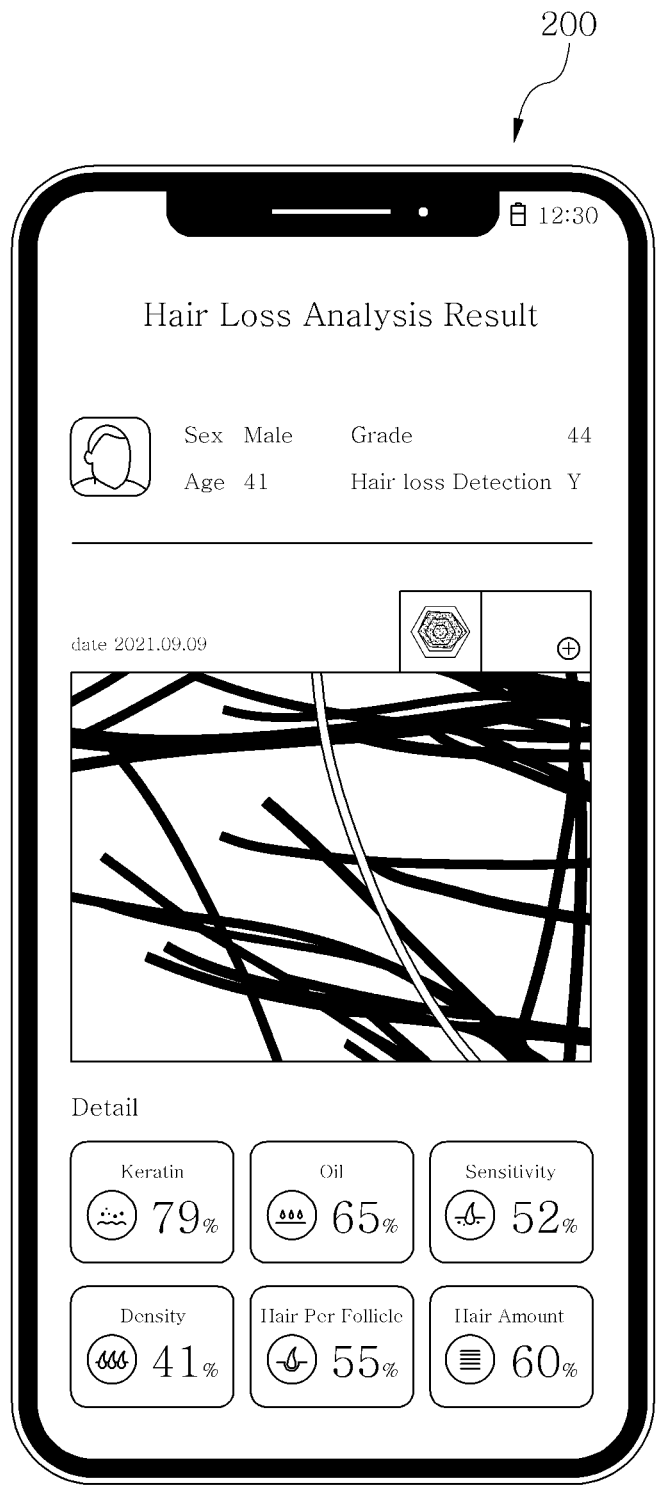
FIG. 3 exemplarily illustrates a scalp analysis result based on a scalp image according to an embodiment.
Figure 4:
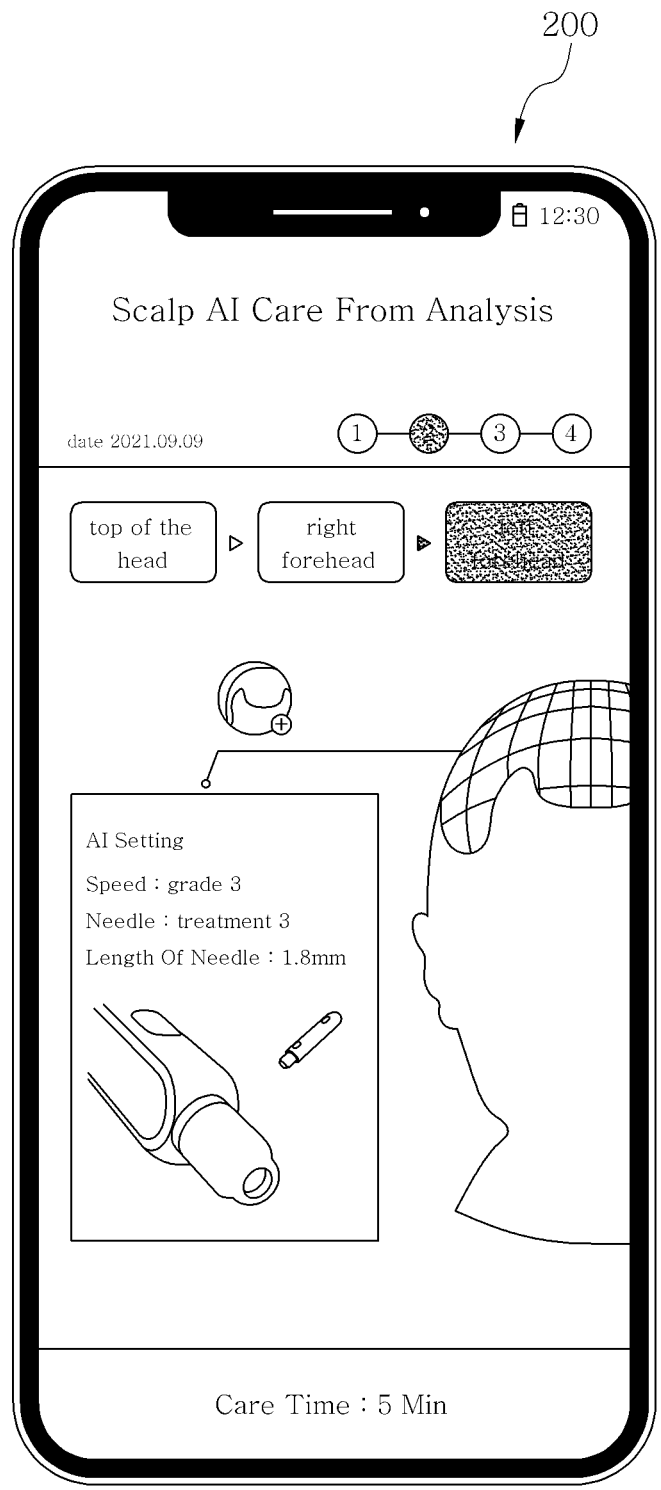
FIG. 4 exemplarily illustrates an operation and setting of an AI-based care program according to an embodiment.

FIG. 3 exemplarily illustrates a scalp analysis result based on a scalp image according to an embodiment. FIG. 4 exemplarily illustrates an operation and setting of an AI-based care program according to an embodiment.

The scalp care solution provision unit 106 may display information about a user's scalp condition diagnosis result through the user terminal. 200 based on the image data acquired through the scalp care device 300. The scalp care solution provision unit 106 may generate information about a diagnosis result of each of the user's front scalp, rear scalp, left side scalp, and right side scalp, and may display the generated information about the scalp condition diagnosis result through the user terminal 200.

The scalp care solution provision unit 106 may display the captured scalp image, information about the user's scalp analysis result, and information about the user's hair analysis result. The user can visually check the scalp image captured through the mobile application installed in the user terminal 200, information about the user's scalp analysis result, and information about the user's hair analysis result.

The scalp care solution provision unit 106 may display detailed items related to the scalp condition. For example, the scalp condition diagnosis unit 102 may display information about keratin and oil contained in the user's scalp, sensitivity, hair density, the number of hairs per pore, etc. through the user terminal 200.

The scalp care solution provision unit 106 may provide a control value for the scalp care device 300 to be controlled by the remote care device control unit 107 through the user terminal 200. For example, the scalp care solution provision unit 106 may display the length and type of the needle suitable for application to the user's left side scalp, a treatment speed, and the like through the user terminal 200.

Figure 5:
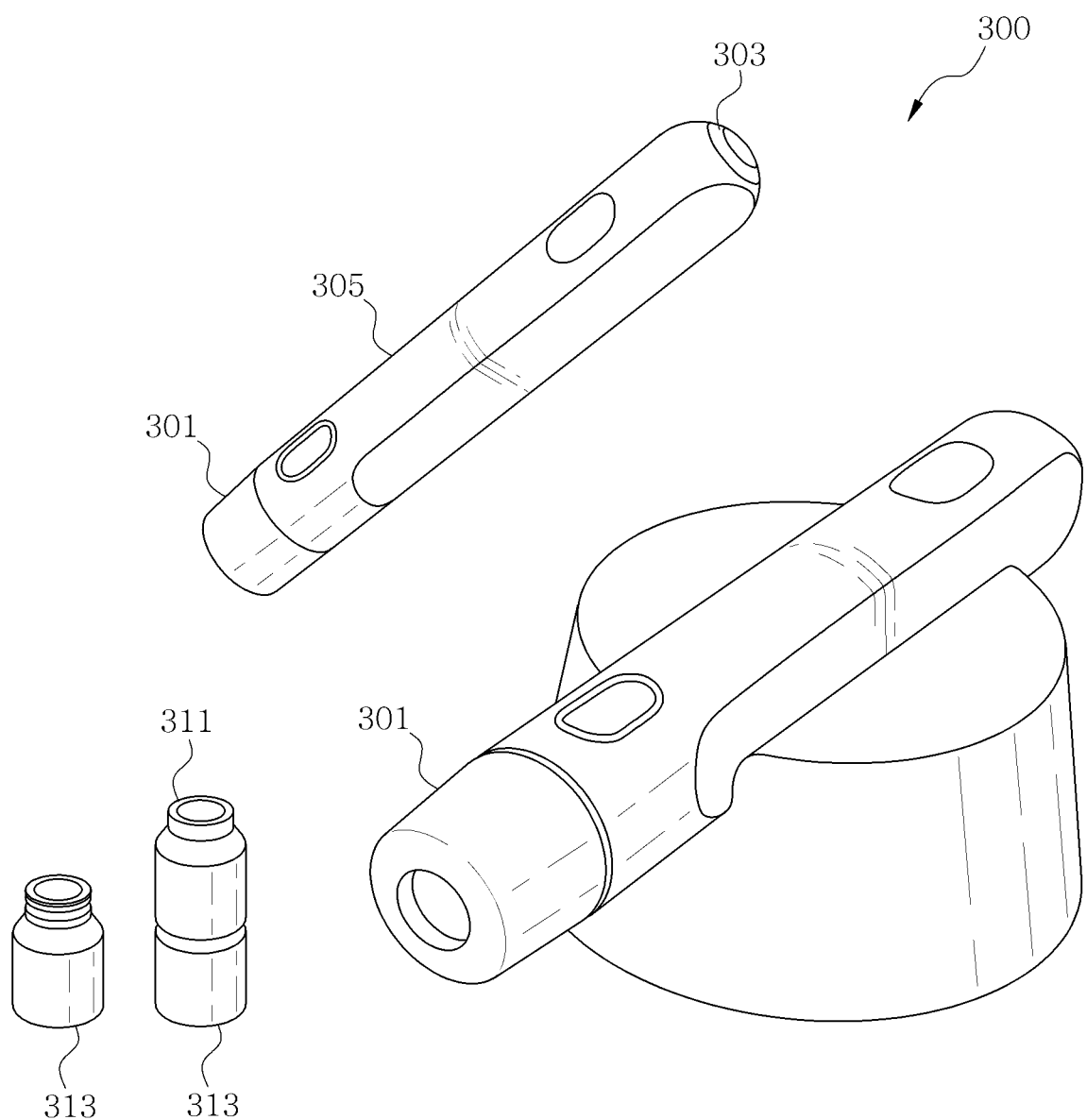
FIG. 5 illustrates a scalp care device interlocked with a scalp management service provision server.

FIG. 5 illustrates the scalp care device 300 interlocked with the scalp management service provision server 100.

The scalp care device 300 includes a photographing part 303 formed on one side in a longitudinal direction and capable of photographing the scalp and may include a care part 301 formed on the other side in the longitudinal direction and capable of stimulating the scalp to effectively care for the scalp; and a grip part 305 formed between the photographing part 303 and the care part 301 such that a user can grip. The scalp care device 300 includes a display, and may display information about a needle length and ampoule amount suitable for the skin thickness for each care location through the display.

The photographing part 303 may include at least one camera module, and the camera module may include at least one lens, image sensor, and image signal processor (ISP), etc. Through an optical lens, equipped with an image automatic correction algorithm, among the at least one lens, the scalp management service provision server 100 may accurately capture and analyze images without irritation to the scalp even in short-distance contact photography. The photographing part 303 may automatically recognize and capture the user's scalp to obtain a scalp image, but may be equipped with an image sensor and/or an illuminance sensor to maintain a constant degree of reflection, thereby acquiring a consistent measurement image and, accordingly, improving accuracy.

The care part 301 may include a needle holder 311 and an ampoule container 313. A needle connected to a customized scalp ampoule cartridge is replaceable and may be hygienically managed. In addition, the needle may be automatically set according to a diagnosed scalp condition and may provide a scalp care solution in three steps through air touch. The needle may be made of or coated with a material with high biocompatibility, such as gold, platinum, silver, titanium, stainless steel, or ceramic. The ampoule container 313 may have an ampoule accommodated therein, and an outlet connected to a portion of the needle holder 311 may be formed on one side of the ampoule container 313. An opening may be formed at one side of the needle holder 311, and a plurality of needles may protrude through the formed opening.

The care unit 301 may include a light output part. The light output part may output light in a direction in which the plurality of needles protrude. Specifically, the light output part may output a low-output light through the opening formed in the needle holder 311. The low-output light may be absorbed by the hair follicle cells of the scalp and activate cellular metabolism to help supply nutrients.

The grip part 305 may include a photographing button for acquiring an image of the user's scalp through the photographing part 303. The grip part may have a cylindrical shape. The grip part may have a shape wherein a central portion of the grip part is concave compared to a distal portion of the grip part so as to improve a user's grip feeling.

FIG. 6 exemplarily illustrates the determination of a hair condition with a hair condition diagnosis unit.

The hair condition diagnosis unit 103 may perform pre-processing on an obtained scalp image to more precisely detect hair from the obtained scalp image. Since a difference in brightness between the scalp and hair is important in detecting hair, the hair condition diagnosis unit 103 may more clearly distinguish the hair from the scalp by making a scalp region to be brighter and a hair region to be darker. The hair condition diagnosis unit 103 may perform contrast stretching to make the scalp region brighter and the hair region darker. The contrast stretching may mean improving and/or emphasizing the contrast (contrast) of the scalp image by digital processing.

The hair condition diagnosis unit 103 may determine the number of hairs included in an image frame constituting the pre-processed scalp image, may calculate a density of hair based on the determined number of hairs, and may generate hair condition information based on the number and density of hairs.

The hair condition diagnosis unit 103 may detect the outline of hair through edge detection based on the image frame. The outline of the hair may be formed of one set of pixels. Since two or more strands of hair can grow from one pore, simply detecting the number of pores may not be sufficient. Therefore, the hair condition diagnosis unit 103 may exclude the hair 11 touching two outer lines of an image frame among hairs whose outlines are detected, and may count the hairs 13 touching one outline of the image frame among the hairs whose outlines are detected.

The hair condition diagnosis unit 103 may detect an end portion of the hair through AI. The hair condition diagnosis unit 103 may determine whether a distal end of the hair corresponds to the pore 15 detected through the scalp condition diagnosis unit 102, may count the hair 13 corresponding to the pore 15 in which the distal end of the hair is detected, and may exclude and may not count the hair 11 whose distal end does not correspond to the pore.

FIG. 7 illustrates a hardware configuration of the scalp management service provision server 100 of FIG. 1.

Referring to FIG. 7, the scalp management service provision server 100 may include at least one processor 110; and a memory for storing instructions that instruct the at least one processor 110 to perform at least one operation.

The at least one operation may include at least some of the above-described operations or functions of the scalp management service provision server 100 and may be implemented in the form of instructions to be performed by the processor 110.

Here, the at least one processor 110 may mean a central processing unit (CPU), a graphics processing unit (GPU), or a dedicated processor where the methods according to embodiments of the present invention are performed. Each of the memory 120 and the storage device 160 may be configured of at least one of a volatile storage medium and a non-volatile storage medium. For example, the memory 120 may be one of a read only memory (ROM) and a random access memory (RAM), and the storage device 160 may be a flash-memory, a hard disk drive (HDD), a solid state drive (SSD), various memory cards (e.g., micro SD card), or the like.

In addition, the scalp management service provision server 100 may include a transceiver 130 for performing communication through a wireless network. In addition, the scalp management service provision server 100 may further include an input interface device 140, an output interface device 150, a storage device 160, and the like. Each of the components included in the scalp management service provision server 100 may be connected by a bus 170 to communicate with each other. FIG. 7 illustrates the scalp management service provision server 100 as an embodiment, but the present invention is not limited thereto. For example, a plurality of user terminals may include the components of FIG. 7.

The methods according to the embodiments of the present disclosure may be implemented in the form of a program command that can be executed through various computer means and recorded in a computer-readable medium. The computer-readable medium can store program commands, data files, data structures or combinations thereof. The program commands recorded in the medium may be specially designed and configured fox the present disclosure ox be known to those skilled in the field of computer software.

Examples of a computer-readable recording medium may include hardware devices such as ROMs, RAMs and flash memories, which are specially configured to store and execute program commands. Examples of the program commands may include machine language code created by a compiler and high-level language code executable by a computer using an interpreter and the like. The hardware devices described above may be configured to operate as at least one software module to perform the operations of the invention, and vice versa.

In addition, the above-described method or apparatus may be implemented by combining all or part of constructions or functions thereof, or the constructions or functions may be separately implemented.

Although the present invention has been described above with reference to the embodiments of the present invention, those skilled in the art may variously modify and change the present invention without departing from the spirit and scope of the present invention as set forth in the claims below.

DESCRIPTION OF SYMBOLS

100: scalp management service provision server
200: user terminal
300: scalp care device

The invention claimed is:

1. A scalp management service provision server for providing a hair loss prevention service and scalp care service for a user, comprising:
    a DB management unit interlocked with the scalp management service provision server and configured to obtain a scalp image of the user from a scalp care device comprising a camera;
    a scalp condition diagnosis unit configured to determine a scalp condition of the user based on the obtained scalp image;
    a hair condition diagnosis unit configured to determine a hair condition of the user based on the obtained scalp image;
    a hair loss diagnosis unit configured to provide a current hair loss progress degree of the user and a hair loss prediction simulation of the user based on the scalp condition and the hair condition;
    a scalp care solution provision unit configured to provide information about a scalp analysis result and hair analysis result of the user through a user terminal of the user; and
    a remote care device control unit configured to remotely control the scalp care device with a control value determined according to the scalp analysis result and hair analysis result of the user.

2. The scalp management service provision server according to claim 1, wherein the scalp care device comprises a photographing part provided in one area of the scalp care device and provided with a camera capable of photographing scalp of the user; a care part provided in another area of the scalp care device and configured to take care of the scalp; and a grip part for gripping by the user, wherein the care part comprises a needle holder comprising a plurality of needles; and an ampoule container, and the grip part comprises a photographing button for obtaining a scalp image of the user through the photographing part.

3. The scalp management service provision server according to claim 1, wherein the hair loss diagnosis unit determines a hair loss improvement result predicted when the user performs recommended guidance provided through the scalp care solution provision unit, and determines a worsened hair loss result of the user predicted when the recommendation guidance is not performed, wherein the recommended guidance provides information about life guidance and scalp care products.

4. The scalp management service provision server according to claim 3, wherein the hair loss diagnosis unit provides a first simulation of performing care and a second simulation of not performing care to the user terminal when the user proceeds with care according to the recommended guidance provided through the scalp care solution provision unit based on a generative adversarial network.

5. The scalp management service provision server according to claim 1, wherein the scalp care solution provision unit lists scalp condition images of the user according to a preset condition, and provides the listed scalp condition images to the user terminal, wherein, when calculating composite scores on a scalp or hair condition corresponding to the scalp condition images, the calculating is performed based on a scalp condition, hair thickness, and hair density of the user, the scalp care solution provision unit provides the determined composite scores to the user terminal.

\* \* \* \* \*